United States Patent [19]

Goto et al.

[11] 4,403,033

[45] Sep. 6, 1983

[54] METHOD FOR PRODUCING L-PHENYLALANINE BY FERMENTATION

[75] Inventors: Eiji Goto, Kawasaki; Masaru Ishihara, Yokohama; Shoji Sakurai, Kawasaki; Hitoshi Enei, Zushi; Koichi Takinami, Yokohama, all of Japan

[73] Assignee: Ajinomoto Company Incorporated, Tokyo, Japan

[21] Appl. No.: 201,369

[22] Filed: Oct. 27, 1980

[30] Foreign Application Priority Data

Oct. 31, 1979 [JP] Japan ............................... 54-140583

[51] Int. Cl.³ ...................... C12P 13/22; C12N 15/00; C12R 1/13; C12R 1/15
[52] U.S. Cl. .................................... 435/108; 435/172; 435/840; 435/843
[58] Field of Search ................ 435/108, 172, 840, 843

[56] References Cited

U.S. PATENT DOCUMENTS

| | | | |
|---|---|---|---|
| 3,660,235 | 5/1972 | Okumura et al. | 435/108 |
| 3,759,790 | 9/1973 | Nakayama et al. | 435/108 |
| 3,909,353 | 9/1975 | Tsuchida et al. | 435/108 |
| 3,917,511 | 11/1975 | Nakayama et al. | 435/108 |

*Primary Examiner*—Lionel M. Shapiro
*Attorney, Agent, or Firm*—Oblon, Fisher, Spivak, McClelland & Maier

[57] ABSTRACT

When sensitivity to decoyinine is given by mutation to L-phenylalanine-producing mutants of the genus Brevibacterium and Corynebacterium, the productivity of L-phenylalanine of the new mutants is improved.

8 Claims, No Drawings

METHOD FOR PRODUCING L-PHENYLALANINE BY FERMENTATION

BACKGROUND OF THE INVENTION

1. Field of the Invention

The present invention relates to a method for producing L-phenylalanine by fermentation.

2. Brief Description of the Prior Art

It is known that tyrosine auxotrophic mutants of the genera Micrococcus and Brevibacterium (Japanese Published Examined Patent Application No. 6345/1952), and mutants of the genera Brevibacterium and Corynebacterium resistant to phenylalanine analogue (U.S. Pat. No. 3,660,235) produce L-phenylalanine. The most efficient known microorganism producer of phenylalanine is *Brevibacterium lactofermentum* AJ 3437 (FERM-P 1914), which is resistant to p-fluorophenylalanine and 5-methyltryptophan and which requires tyrosine and methionine for growth. This strain produced 2.20 g/dl phenylalanine from 13 g/dl glucose. However, the yield of phenylalanine in this best known method is still insufficient to fulfill commercial requirements. Therefore, a need continues to exist for a method for the production of phenylalanine by fermentation in high yields.

SUMMARY OF THE INVENTION

It is an object of the present invention to provide a method for the production of phenylalanine by fermentation in high yields.

This object of the present invention which will hereinafter become more readily apparent has been attained by providing a method for producing L-phenylalanine by fermentation which comprises culturing aerobically in a culture medium mutant belonging to the genus Brevibacterium or Corynebacterium, being sensitive to decoyinine and being capable of producing L-phenylalanine, and recovering the L-phenylalanine accumulated in the culture medium.

DESCRIPTION OF THE PREFERRED EMBODIMENTS

The mutants employed in the present invention belong to the genus Brevibacterium or Corynebacterium, are sensitive to decoyinine, are capable of producing L-phenylalanine, and can be induced by conventional mutagenesis from known mutants capable of producing L-phenylalanine or wild strains of the genus brevibacterium or Corynebacterium.

When a wild strain is used as the parent strain, L-phenylalanine productivity is given to the wild strain either prior to giving sensitivity to decoyinine or after giving sensitivity to decoyinine. In order to give L-phenylalanine productivity to the wild strains or mutants sensitive to decoyinine, tyrosine-auxotrophic mutant or a mutant resistant to phenylalanine-analogue is induced as is known. The phenylalanine-analogues of this invention inhibit the growth of the microorganisms of the genus Brevibacterium and Corynebacterium, and the inhibition is suppressed partly or completely when L-phenylalanine coexists in the medium. Examples of the phenylalanine-alalogues are $\beta$-amino-$\beta$-phenylprionic acid, o-fluorophenylalanine, m-fluorophenylalanine, p-fluorophenylalalnine, $\beta$-2-thienylalanine, $\beta$-3-thienylalanine, $\beta$-2-furylalanine, $\beta$-3-furylalanine, o-aminophenylalanine, m-phenylalanine, p-aminophenylalanine, $\alpha$-amino-$\beta$-phenylalanine sulfonate, $\beta$-2-phrolalanine, 1-cyclopentene-1-alanine, 1-cyclohexene-1-alanine, $\beta$-4-pyridinylalanine, $\beta$-4-pyrazolealanine, p-nitrophenylalanine, $\beta$-4-thiazolealanine, cyclohexylalanine, 2-amino-4-methyl-4-hexenoic acid, S-(1,2-dichlorovinyl)-cysteine, o-chlorophenylalanine, m-chlorophenylalanine, p-chlorophenylalanine, o-bromophenylalanine, m-bromophenylalanine, and p-bromophenylalanine.

The wild strains mentioned above are the so-called "Coryne-form glutamic acid producing bacteria" and the preferred examples are:

*Brevibacterium divaricatum* ATCC 14020
*Brevibacterium flavum* ATCC 14067
*Brevibacterium lactofermentum* ATCC 13869
*Brevibacterium roseum* ATCC 13825
*Brevibacterium saccharolyticum* ATCC 14066
*Corynebacterium acetoacidophilum* ATCC 13870
*Corynebacterium acetoglutamicum* ATCC 15806
*Corynebacterium glutamicum* ATCC 13032

Specimens of the mutant of the present invention are:
Brevibacterium lactofermentum AJ 11474, FERM-P 5247, NRRL B-12270 (5-MT$\gamma$, PFP$\gamma$, Met$^-$, Dec$^s$)
Brevibacterium lactofermentum AJ 11475, FERM-P 5248, NRRL B-12271 (5-MT$\gamma$, PFP$\gamma$, Met$^-$, Dec$^s$, Tyr$^-$)
Brevibacterium flavum AJ 11476, FERM-P 5249, NRRL B-12269 (PFP$\gamma$, Dec$^s$)
Corynebacterium acetoacidophilum AJ 11477, FERM-P 5250, NRRL B-12272 (PEP$\gamma$, Dec$^s$)

5-MT$\gamma$: Resistant to 5-methyl-tryptophan.
PFP$\gamma$: Resistant to p-fluoro-phenylalanine.
Met$^-$: Methionine auxotroph.
Tyr$^-$: Tyrosine auxotroph.
Dec$^s$: Sensitive to decoyinine.

The mutants of the present invention can be induced from the parent strains by conventional mutagens such as exposure to N-methyl-N'-nitro-N-nitrosoguanidine.

Mutant sensitive to decoyinine in the present invention gives lower relative growth than its parent when it is cultured in a medium containing decoyinine. The relative growth is the ratio of the growth in a medium containing decoyinine to the growth in a medium free from decoyinine.

The relative growth of preferred mutants is less than 50% in a medium containing 100 $\mu$g/ml decoyinine, in which the relative growth of their parents is more than 80%.

The media used to culture the mutants of the present invention are conventional and contain a carbon source, a nitrogen source, and inorganic ions, and when required contain minor organic nutrients such as amino acid and vitamine. As the carbon source, carbohydrates such as glucose, sucrose, fructose and maltose, molasses and starch hydrolysate containing these carbohydrates, organic acids such as citric acid and acetic acid, and alcohols such as ethanol can be used. Ammonium salts, nitrate salts, aqueous ammonia, gaseous ammonia and urea can be used as the nitrogen source. As the inorganic ions, potassium salts, phosphate salts, magnesium salts and so on are added to the media when required.

When the mutant requires tyrosine for growth, tyrosine is added to the media.

Cultivation is carried out under an aerobic condition, adjusting the pH of the medium to 5 to 9, and the temperature to 20° to 40° C. Cultivation is continued for 1 to 4 days, whereby L-phenylalanine is accumulated in the medium.

The L-phenylalanine accumulated in the culture medium can be recovered by conventional means, such as adjusting the pH of the culture broth to the isoelectric point of phenylalanine after removing cells, and using ion-exchange resins.

EXAMPLE 1

Cells of *Brevibacterium lactofermentum* AJ 11473 (FERM-P 5246) (5-MT$\gamma$, PFP$\gamma$, Met$^-$) were exposed to 250 $\mu$g/ml N-methyl-N'-nitro-N-nitrosoguanidine at 25° C. for 30 minutes, and screened for mutants which became sensitive to decoyinine. Among the mutants, the best L-phenylalanine producer, AJ 11474, was selected.

In an analogous manner to the above, AJ 11475, AJ 11476 and AJ 11477 were derived from *Brevibacterium lactofermentum* FERM-P 1914 (Tyr$^-$, PFP$\gamma$, 5-MT$\gamma$, Met$^-$; derived from AJ 11473), *Brevibacterium flavum* ATCC 14067 and *Corynebacterium acetoacidophilum* ATCC 13870, respectively.

Relative growth of the above-mentioned strains was tested in an aqueous medium, and is shown in Table 1.

TABLE 1

| Decoyinine added $\mu$g/ml | Relative Growth (%) | | | | | | |
|---|---|---|---|---|---|---|---|
| | AJ 11473 | AJ 11474 | AJ 11475 | ATCC 14067 | AJ 11476 | ATCC 13870 | AJ 11477 |
| 0 | 100 | 100 | 100 | 100 | 100 | 100 | 100 |
| 50 | 91 | 58 | 60 | 93 | 53 | 96 | 59 |
| 100 | 82 | 45 | 42 | 85 | 41 | 88 | 38 |
| 200 | 61 | 28 | 25 | 60 | 23 | 67 | 25 |
| 500 | 32 | 9 | 10 | 35 | 10 | 39 | 12 |
| 1000 | 16 | 3 | 4 | 21 | 5 | 25 | 3 |

Experimental method: a basal medium was prepared to contain, per liter, 20 g glucose, 2.0 g urea, 15 g $(NH_4)_2SO_4$, 1.0 g $KH_2PO_4$, 3.0 g $K_2HPO_4$, 0.1 g $MgSO_4.7H_2O$, 50 $\mu$g biotin, 100 $\mu$g thiamine.HCl, 150 mg L-tyrosine in the medium for AJ 11475, 0.3 g DL-methionine in the media for AJ 11473, AJ 11474 and AJ 11475, 10 mg $FeSO_4.7H_2O$, and 10 mg $MnSO_4.4H_2O$, and thereafter adjusted to pH 7.0. Three ml portions of the basal medium were placed in test tubes, and the amounts of decoyinine shown in Table 1 were added.

The medium was inoculated with $5 \times 10^7$/ml cells well-washed with the basal medium. The cultivation was carried out for 24 hours at 30° C. Optical density of the resulted medium at 562 m$\mu$ was measured to determine the growth.

EXAMPLE 2

An aqueous culture medium was prepared to contain 13 g/dl glucose, 1.0 g/dl $(NH_4)SO_4$, 1.5 g/dl $KH_2PO_4$, 0.04 g/dl $MgSO_4.7H_2O$, 5.0 $\mu$g/dl biotin, 20.0 $\mu$g/dl thiamine.HCl, 1 mg/dl $FeSO_4.7H_2O$, 1 mg/dl $MnSO_4.4H_2O$, 40 mg/dl L-tyrosine (in the medium for AJ 11475), 40 mg/dl DL-methionine (in the media for AJ 11473, AJ 11474 and AJ 11475), 3.0 ml/dl soy-protein-hydrochloric acid-hydrolysate, 1.2 g/dl fumaric acid, 0.3 ml/dl acetic acid, and 5.0 g/dl $CaCO_3$, and adjusted to pH 7.0. Twenty ml portions of the medium were placed in 50 ml shaking flasks, and heated to sterilize. One loopful of inoculum of the microorganisms listed in Table 2 was introduced into each medium and cultured at 30° C. for 72 hours with shaking.

The amount of L-phenylalanine accumulated in the resultant culture liquids are shown in Table 2.

TABLE 2

| Microorganism | L-phenylalanine accumulated (g/dl) |
|---|---|
| AJ 11473 | 2.00 |
| AJ 11474 | 2.45 |
| AJ 11475 | 2.48 |
| AJ 11476 | 1.80 |
| AJ 11477 | 1.70 |

EXAMPLE 3

A seed culture medium (50 ml) of pH 7.0 containing, per deciliter, 3 g glucose, 0.1 g $KH_2PO_4$, 0.04 $MgSO_4.7H_2O$, 1 mg $FeSO_4.7H_2O$, 1 mg $MnSO_4.4H_2O$, 40 mg L-tyrosine, 40 mg DL-methionine, 5 ml soybean protein hydrolysate, 10 $\mu$g biotin, 30 $\mu$g thiamine.HCl and 0.2 g urea was placed in a 500 ml shaking flask, and inoculated with *Brevibacterium lactofermentum* AJ 11474. Cultivation was carried out at 31.5° C. for 16 hours.

Three hundred ml of a medium of pH 7.0 containing, per deciliter, 0.4 g ammonium acetate, 0.4 g sodium acetate, 0.01 g $KH_2PO_4$, 0.04 g $MgSO_4.7H_2O$, 1 mg $FeSO_4.7H_2O$, 1 mg $MnSO_4.4H_2O$, 40 mg DL-methionine, 5 ml soybean protein hydrolysate, 10 $\mu$g biotin, 30 $\mu$g thiamine.HCl, and 0.2 g urea was placed in an 1 l-fermentation vessel, and sterilized.

Fifteen ml of the seed culture broth mentioned above was transferred into a fermentation vessel, and cultivation was carried out at 31.5° C. agitating at 1200 $\gamma$.p.m, while aerating at 300 ml/minute. After 3 hours of cultivation, 70% acetic acid solution and gaseous ammonia were fed so as to maintain the pH of the medium at from 7.0 to 7.7.

After 40 hours of cultivation, 55 g acetic acid had been consumed, and 2.50 g/dl L-phenylalanine had accumulated in the culture medium.

What is claimed is:

1. A method for producing L-phenylalanine which comprises culturing a mutant belonging to the genus Brevibacterium or Corynebacterium, sensitive to decoyinine and capable of producing L-phenylalanine, and recovering the L-phenylalanine accumulated in the culture medium.

2. The method of claim 1, wherein said mutant belongs to the species *Brevibacterium divaricatum*, *Brevibacterium flavum*, *Brevibacterium lactofermentum*, *Brevibacterium roseum*, *Brevibacterium saccharolyticum*, *Corynebacterium acetoacidophilum*, *Corynebacterium glutamicum* or *Corynebacterium acetoglutamicum*.

3. The method of any of claims 1 or 2, wherein the relative growth of said mutant is less than fifty percent in an aqueous medium containing 100 $\mu$g/ml of decoyinine, in which the relative growth of the parent of said mutant being more than eighty percent.

4. The method of any of claims 1 or 2, wherein said mutant requires L-tyrosine for growth.

5. The method of claim 1 or 2, wherein said mutant is resistant to a phenylalanine-analogue.

6. The method of claim 3, wherein said mutant requires L-tyrosine for growth.

7. The method of claim 3, wherein said mutant is resistant to a phenylalanine-analog.

8. The method of claim 6, wherein said mutant is resistant to a phenylalanine-analog.